(12) United States Patent
Noda et al.

(10) Patent No.: US 9,377,427 B2
(45) Date of Patent: Jun. 28, 2016

(54) PARTICULATE MATTER SENSOR

(75) Inventors: Masafumi Noda, Fujisawa (JP); Tadashi Uchiyama, Fujisawa (JP); Mitsuhiro Aso, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 304 days.

(21) Appl. No.: 14/117,098

(22) PCT Filed: Apr. 27, 2012

(86) PCT No.: PCT/JP2012/061369
§ 371 (c)(1),
(2), (4) Date: Nov. 12, 2013

(87) PCT Pub. No.: WO2012/160949
PCT Pub. Date: Nov. 29, 2012

(65) Prior Publication Data
US 2014/0157881 A1    Jun. 12, 2014

(30) Foreign Application Priority Data
May 20, 2011    (JP) .................................. 2011-113539

(51) Int. Cl.
*G01N 27/22*    (2006.01)
*G01M 15/10*    (2006.01)
*F01N 3/022*    (2006.01)
*G01N 15/06*    (2006.01)
(Continued)

(52) U.S. Cl.
CPC .............. *G01N 27/22* (2013.01); *F01N 3/0222* (2013.01); *F01N 13/008* (2013.01); *G01M 15/102* (2013.01); *G01N 15/0656* (2013.01); *F01N 2560/05* (2013.01); *F01N 2560/12* (2013.01); *G01N 2015/0046* (2013.01); *Y02T 10/20* (2013.01)

(58) Field of Classification Search
CPC . G01N 15/0656; G01N 15/102; G01N 27/22; G01N 2015/0046; F01N 3/0222; F01N 13/008; F01N 2560/05; F01N 2560/12; Y02T 10/20
See application file for complete search history.

(56) References Cited

FOREIGN PATENT DOCUMENTS

| JP | 2010-144630 | 7/2010 |
|----|-------------|--------|
| JP | 2011-12577  | 1/2011 |

(Continued)

OTHER PUBLICATIONS

Written Opinion of the International Searching Authority mailed Jun. 26, 2012 in corresponding International Application No. PCT/JP2012/061369.

(Continued)

*Primary Examiner* — Daniel S Larkin
(74) *Attorney, Agent, or Firm* — Staas & Halsey LLP

(57) ABSTRACT

A diesel particulate filter ("DPF") including vertically and horizontally stacked cells in which all of vertical and horizontal sides are surrounded by walls formed of a porous material, and sealing end faces of the cells alternately vertically and horizontally are provided with first and second electrodes. In a particulate matter ("PM") sensor in which a PM deposit quantity of the DPF is detected by a capacitance of a capacitor formed by the first and second electrodes, among open cells, the first electrodes are inserted into the open cells arranged in a line in a diagonal direction, and the second electrodes are inserted into the open cells arranged in a line in the diagonal direction and including the open cells secondarily adjacent to each of the open cells into which the first electrodes are inserted.

11 Claims, 9 Drawing Sheets

(51) Int. Cl.
  *F01N 13/00* (2010.01)
  *G01N 15/00* (2006.01)

(56) References Cited

FOREIGN PATENT DOCUMENTS

| JP | 2011-12578 | 1/2011 |
| WO | WO 93/08382 | 4/1993 |
| WO | WO 2007/066462 A1 | 6/2007 |
| WO | WO 2011/001825 A1 | 1/2011 |

OTHER PUBLICATIONS

Patent Abstracts of Japan, Publication No. 2010-144630, Published Jul. 1, 2010.
Patent Abstracts of Japan, Publication No. 2011-012577, Published Jan. 20, 2011.
International Search Report mailed Jun. 26, 2012 in corresponding International Application No. PCT/JP2012/061369.

PARTICULATE MATTER SENSOR

CROSS-REFERENCE TO RELATED APPLICATIONS

This application is a U.S. national stage application of PCT/JP2012/061369 filed Apr. 27, 2012 and claims foreign priority benefit of Japanese Patent Application No. 2011-113539 filed May 20, 2011 in the Japanese Patent Office, the contents of both of which are incorporated herein by reference.

TECHNICAL FIELD

The present invention relates to a particulate matter (PM) sensor which can detect an average PM deposit quantity of an entire diesel particulate filter ("DPF") and at the same time can ensure a capacitance large enough for detection.

BACKGROUND ART

In a vehicle equipped with an internal combustion engine, a DPF is installed in an exhaust gas passage from the internal combustion engine to the atmosphere, and PM is caught by the DPF. The DPF is a member which temporarily catches the PM on a filter formed of porous ceramics and having a shape of a honeycomb pore.

If the amount of the PM caught by the DPF (hereinafter referred to as a PM deposit quantity) increases, the exhaust pressure of the internal combustion engine increases to lower the characteristics of the internal combustion engine, and therefore, processing for burning the caught PM is performed. This processing is referred to as DPF regeneration. In the DPF regeneration, fuel injection is performed to increase an exhaust temperature. When the exhaust temperature increases, the temperature of the DPF is increased, and the PM caught by the DPF is burned.

At that time, when the PM deposit quantity is too large, the DPF is damaged by heat generated in the DPF regeneration. In order to perform the DPF regeneration before the PM deposit quantity increases too much, the PM deposit quantity is required to be accurately detected.

As the PM sensor detecting the PM deposit quantity, there has been known a PM sensor in which two electrodes are installed in the DPF, and the PM deposit quantity is detected from a capacitance of a capacitor formed by the two electrodes. In this type of PM sensor, since the PM as a mixture of a dielectric with a conductor is deposited between electrodes, the capacitance increases linearly with respect to the PM deposit quantity.

In a conventional PM sensor 81 illustrated in FIG. 8, two electrodes 83 and 84 formed into a half-divided cylindrical shape are installed on an outer circumference of a columnar DPF 82. The two electrodes 83 and 84 face each other with the DPF 82 provided between the electrodes 83 and 84, whereby the capacitance of the capacitor formed by the two electrodes 83 and 84 is changed according to the PM deposit quantity of the entire DPF 82 (Patent Document 1).

In a conventional PM sensor 91 illustrated in FIG. 9, one electrode 93 is installed on an outer circumference of a columnar DPF 92, having a housing 95, and the other electrode 94 is concentrically installed inside the electrode 93. The capacitance of the capacitor formed by the two electrodes 93 and 94 is changed according to the PM deposit quantity of a portion of the DPF 92 (Patent Document 2).

PRIOR ART DOCUMENTS

Patent Document 1: Japanese Patent Laid-Open Publication No. 2010-144630

Patent Document 2: Japanese Patent Laid-Open Publication No. 2011-012577

However, in general, a DPF is stored in a metal housing used for protecting the DPF, and the housing is attached to a vehicle body. Thus, a capacitor is formed between an electrode installed at an outer circumference of the DPF and the housing.

In the PM sensor 81 of FIG. 8, since a distance between the electrodes 83 and 84 and the housing 85 is notably shorter than a distance between the two electrodes 83 and 84, the capacitance of the capacitor formed by the electrodes 83 and 84 and the housing 85 is notably larger than the capacitance of the capacitor formed by the electrodes 83 and 84. Further, the capacitance of the capacitor formed by the two electrodes 83 and 84 and the housing 85 is thermally and mechanically unstable. Consequently, in a circuit of the PM sensor 81, the capacitor constituted of the two electrodes 83 and 84 and the housing 85 is connected in parallel to the capacitor constituted of the two electrodes 83 and 84. When a capacitor in which the PM deposit quantity should be detected is connected in parallel to a capacitor whose capacitance is notably larger than the capacitor concerned and at the same time unstable, the PM deposit quantity cannot be accurately detected.

In the PM sensor 91 of FIG. 9, the capacitance of the capacitor formed by the two electrodes 93 and 94 is increased by reducing a distance between the outer circumferential electrode 93 and the inner electrode 94. However, this requires that the inner electrode 94 is disposed near the outer circumference of the DPF 92, so that a portion of the PM deposit quantity of the DPF 92 provided on the inner side than the inner electrode 94 cannot be detected. When only a portion of the PM deposit quantity of the DPF 92 provided on the outer side than the inner electrode 94 is detected, the detected value may differ from an average PM deposit quantity of the entire DPF 92.

SUMMARY OF THE INVENTION

Thus, in order to solve the above problem, an object of the present invention is to provide a PM sensor which can detect an average PM deposit quantity of the entire DPF and at the same time can secure a capacitance large enough for detection.

In order to achieve the above object, in a PM sensor of the present invention, first and second electrodes are provided in a DPF obtained by vertically and horizontally stacking cells in which all of vertical and horizontal sides are surrounded by walls formed of a porous material and sealing end faces of the cells alternately vertically and horizontally, and in a PM sensor which detects a deposit quantity of the DPF from a capacitance formed by the first and second electrodes, among cells which are not sealed (hereinafter referred to as open cells), the first electrodes are inserted into the open cells arranged in a line in a diagonal direction, and the second electrodes are inserted into the open cells arranged in a line in the diagonal direction and including the open cells secondarily adjacent to each of the open cells into which the first electrodes are inserted.

The present invention exhibits the following excellent effects.

1) An average PM deposit quantity of the entire DPF can be detected.
2) A capacitance large enough for detection can be secured.

DETAILED DESCRIPTION

Hereinafter, embodiments of the present invention will be described with reference to the accompanying drawings.

First, the structure and function of a DPF will be described as it relates to the present invention.

Figure 1:
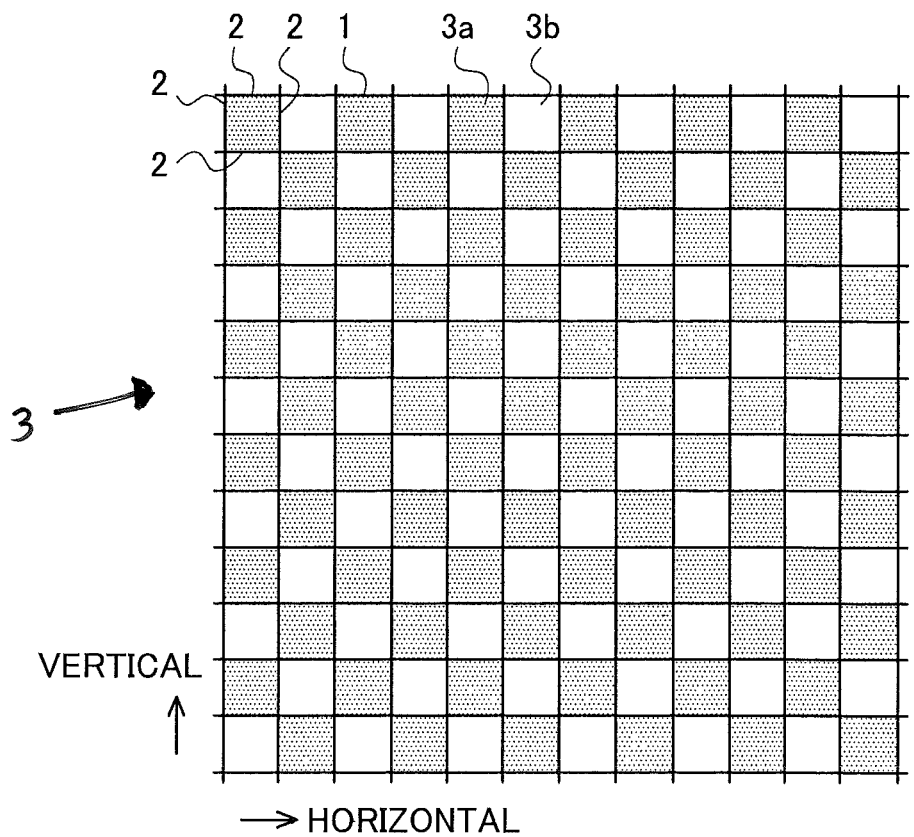
FIG. 1 is a partial end face view of a DPF to which the present invention is applied.

As illustrated in FIG. 1, the DPF 1 is obtained by vertically and horizontally stacking cells 3 in which all of vertical and horizontal sides are surrounded by walls 2 formed of a porous material and sealing end faces of alternate cells 3 vertically and horizontally. In the drawing, the sealing is illustrated by hatching. Among the cells 3, the sealed cells are referred to as sealed cells 3a, and the cells which are not sealed are referred to as open cells 3b. As illustrated, the cells vertically adjacent to the sealed cell 3a and the cells horizontally adjacent to the sealed cells 3a are the open cells 3b, and the cells vertically adjacent to the open cell 3b and the cells horizontally adjacent to the open cell 3b are the sealed cells 3a. Although an end face shape of the cell 3 is a square in this embodiment, any shape, such as a rectangle shape or a parallelogram, may be employed as long as the shapes can be continuously arranged.

The sealing and the opening are reversed in an end face at one side and an end face at the opposite side. Namely, in the cell 3, when the end face at one side is sealed, the end face at the opposite side is surely open, and when the end face at one side is open, the end face at the opposite side is surely sealed. Accordingly, regarding the same cell 3, when the cell 3 is seen from one side, the cell 3 is the sealed cell 3a, and when the cell 3 is seen from the opposite side, the cell 3 is the open cell 3b.

Figure 2:
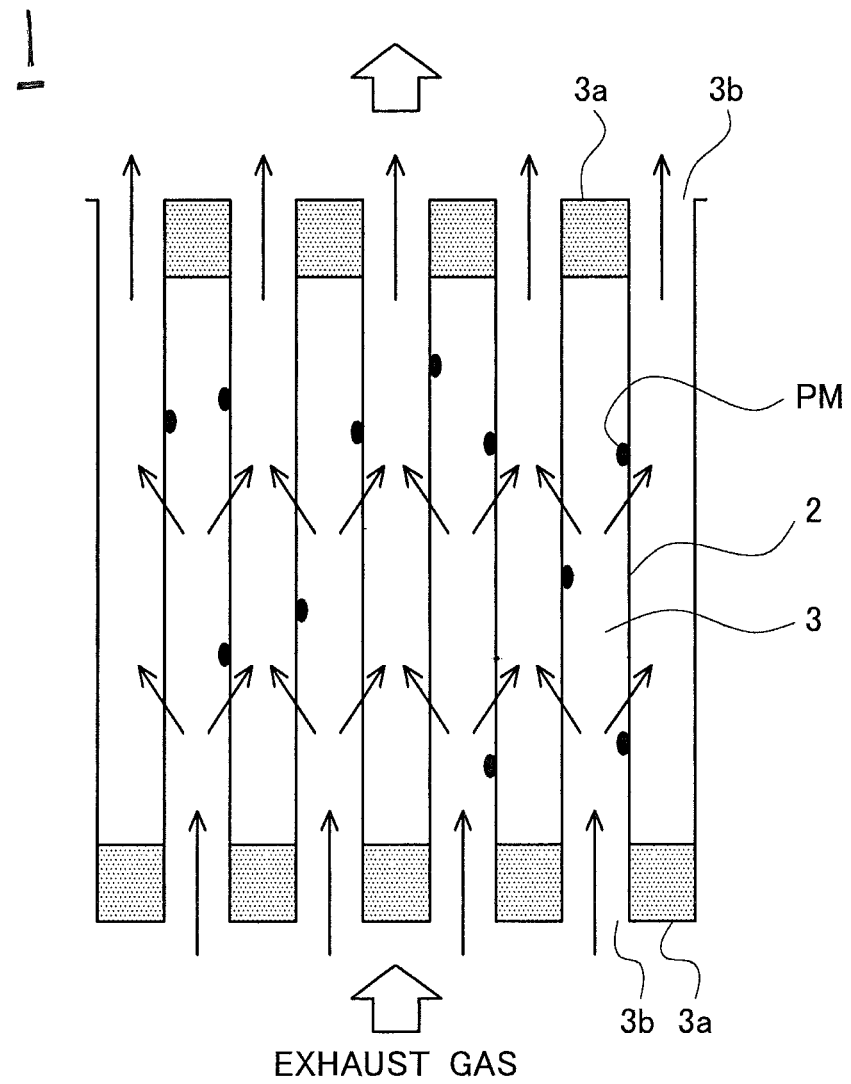
FIG. 2 is a partial sectional side view of the DPF to which the invention is applied.

As illustrated in FIG. 2, the DPF 1 is installed in an exhaust gas passage, and any one of the end faces of the DPF faces the upstream side, and the end face at the opposite side faces the downstream side. In the end face facing the upstream side, an exhaust gas does not flow into the sealed cells 3a, and the exhaust gas flows into only the open cells 3b. The open cells 3b into which the exhaust gas has flowed is sealed at the opposite end face of the cell 3 facing the downstream, and therefore, the exhaust gas passes through the wall 2 formed of a porous material and moves to the adjacent sealed cell 3a. In the adjacent sealed cell 3a, since the opposite end face facing the downstream is open and consequently becomes the open cell 3b, the exhaust gas flows out from the open cell 3b. In this way, when the exhaust gas passes through the wall 2, the PM in the exhaust gas is attracted to the wall 2 formed of the porous material. In FIG. 2, although the exhaust gas having flowed into the open cell 3b moves to the adjacent two sealed cells 3a, since the exhaust gas having flowed into the open cell 3b actually moves to the four sealed cells 3a vertically and horizontally adjacent to each other, the PM is attracted to the four vertical and horizontal walls 2.

Figure 3:
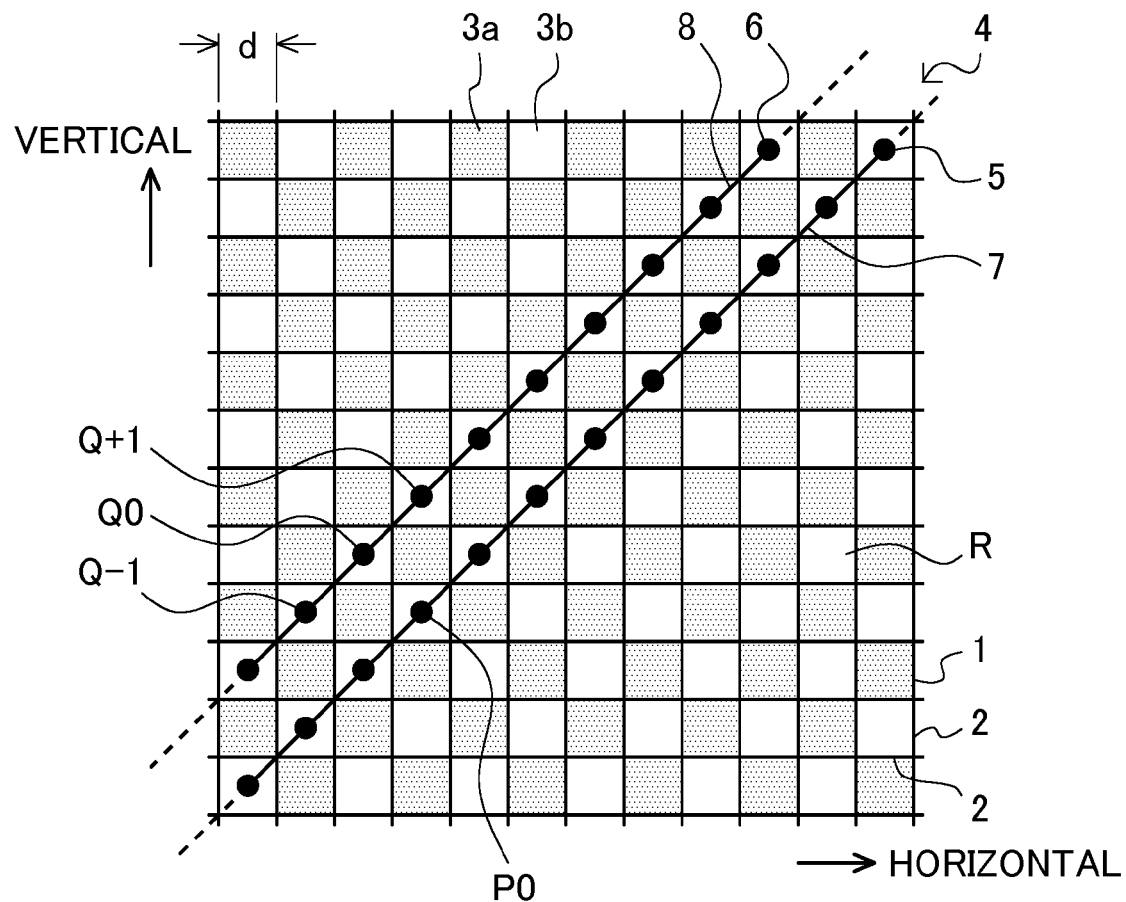
FIG. 3 is a partial end face view of the DPF to which a PM sensor, of the present invention is attached.

In the PM sensor 4 illustrated in FIG. 3, first and second electrodes 5 and 6 are provided in the DPF 1, and the PM deposit quantity of the DPF 1 is detected by the capacitance of a capacitor formed by the first and second electrodes 5 and 6.

In the PM sensor 4, the first electrodes 5 are inserted into the open cells 3b arranged in a line in a diagonal direction among all the open cells 3b, and the second electrodes 6 are inserted into the open cells 3b which are adjacent to the open cells 3b into which the first electrodes 5 are inserted and arranged in a line in the diagonal direction. Since the open cells 3b are arranged alternately with the sealed cells 3a, the open cells 3b adjacent to the open cells 3b are the open cells 3b adjacent to each other by skipping over the sealed cell 3a in the vertical and horizontal directions.

The electrodes 5 and 6 inserted into the open cells 3b are metal wires, for example. The first electrodes 5 inserted into the open cells 3b arranged in a line are short-circuited to each other by a short circuiting line 7. Similarly, the second electrodes 6 inserted into other open cells 3b arranged in a line are short-circuited to each other by another short circuiting line 8. Although a depth that the electrodes 5 and 6 are inserted from the end face may be any depth, the deeper the electrodes 5 and 6 are inserted, the larger each length of the electrodes 5 and 6 is, and this contributes to the increase of the facing area of the electrodes. Accordingly, for example, the electrodes 5 and 6 preferably reach near a sealed portion of the opposite end face of the open cell 3b.

Although the end face into which the electrodes 5 and 6 are inserted may be an end face facing the upstream of the exhaust gas passage or an end face facing the downstream, the electrodes 5 and 6 are inserted into the same end face.

In the PM sensor 4 of FIG. 3, with regard to an electrode P0 among the first electrodes 5, the second electrode 6 closest to the electrode P0 is an electrode Q0 on a diagonal line intersecting with a line formed by the first electrodes 5, and when a pitch (vertical and horizontal widths) of the cell 3 is d, a distance between the electrodes P0 and Q0 is $\sqrt{2}d$. Thus, the distance between electrodes is $\sqrt{2}d$ by the electrodes P0 and Q0, and a capacitor having a facing area of the electrodes proportional to an electrode diameter is formed. The second electrodes 6 which are next closest to the electrode P0 are electrodes Q+1 and Q−1 positioned immediately near the electrode Q0 on a line formed by the second electrodes 6, and a distance between the electrode P0 and the electrodes Q±1 is 2d. The distance between electrodes is 2 d by the electrodes P0 and the electrodes Q±1, and two capacitors each having the facing area of the electrodes proportional to the electrode diameter are formed. Similarly, the capacitors are constituted of the third and subsequent first electrodes 5 counted from the electrode P0 and the sequentially closest second electrodes 6. In the capacitor obtained by integrating them and formed by the first electrodes 5 and the second electrodes 6, the distance between electrodes is $\sqrt{2}d$, and the capacitor can be regarded as a parallel plane plate capacitor having a predetermined facing area of the electrodes and formed by two electrode plates.

In the capacitor formed by the first electrodes 5 and the second electrodes 6, since the distance between electrodes is $\sqrt{2}d$ and that is small in comparison with the conventional PM sensors 81 and 91, the capacitance is large. Further, since the electrodes 5 and 6 are separated from the housing, the influence of the housing can be expected to be reduced.

In the PM sensor 4, although the metal wires as the electrodes 5 and 6 are inserted into the open cells 3*b*, the inserted metal wire is required to have a wire diameter large enough to be durable against the high temperature when the DPF is regenerated and mechanical vibration generated when a vehicle is running. The wire diameter is determined to be as large as possible, considering the thickness of the wall 2 with respect to the pitch d of the cell 3 and a clearance.

Figure 4:
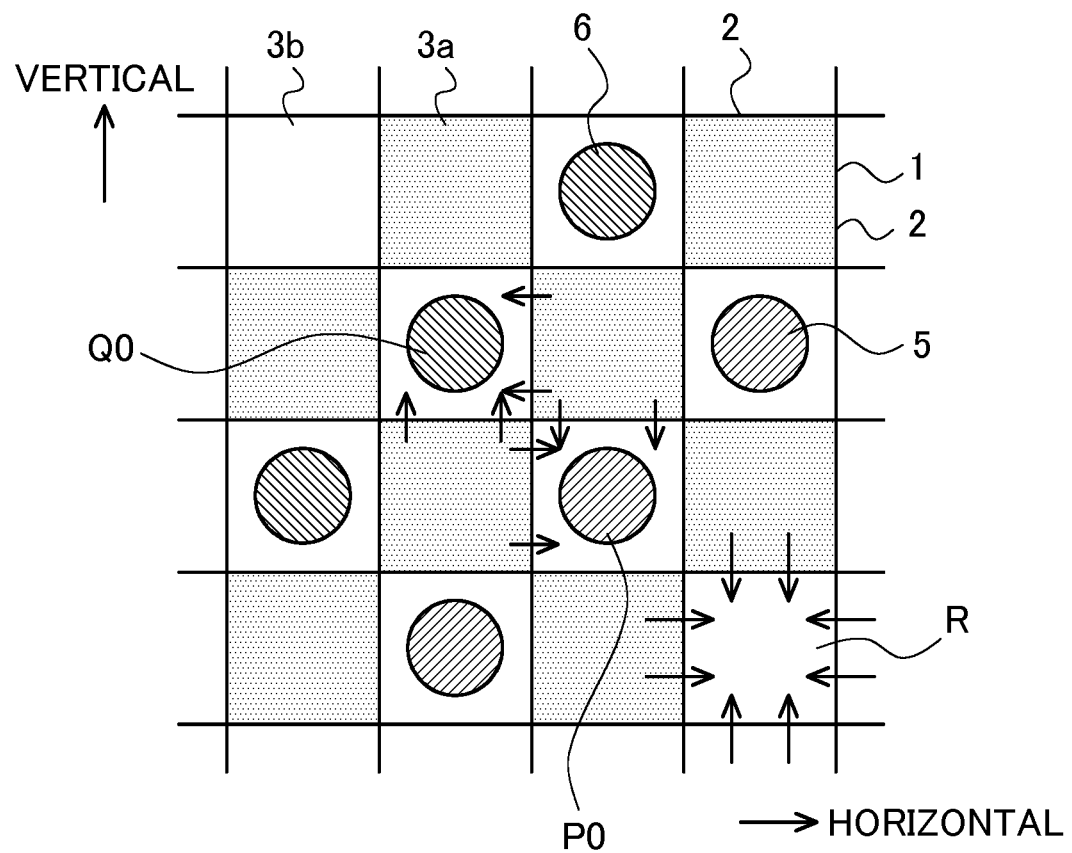
FIG. 4 is an enlarged view of a relevant portion of FIG. 3.

FIG. 4 illustrates a further enlarged view of the end face of the DPF 1.

In the open cells 3*b* of the electrodes P0 and Q0 amongst the open cells 3*b* into which the electrodes 5 and 6 are inserted, a flow of exhaust gas passing through the wall 2 and flowing into the open cells 3*b* from the sealed cells 3*a* is illustrated by arrows. The arrows are arrows of the sectional side view of FIG. 2 as viewed from the end face. However, in fact, although the exhaust gas passes through the four vertical and horizontal walls 2 and flows into the open cell 3*b* from the four vertical and horizontal sealed cells 3*a*, in this example the arrows are illustrated with respect to only the walls 2 located inside the capacitor formed by the electrodes 5 and 6 (between electrode plates). As described above, when the exhaust gas passes through the wall 2, the PM is attracted on the wall 2, and therefore, the PM is deposited on the wall 2 between the electrodes P0 and Q0. Similarly, the exhaust gas flows from the four vertical and horizontal sealed cells 3*a* into a general open cell R into which the electrodes 5 and 6 are not inserted, and the PM is deposited on each of the four vertical and horizontal walls 2.

At that time, in the open cells 3*b* of the electrodes P0 and Q0, the electrodes 5 and 6 are inserted; therefore, the cross-sectional area effective as a flow passage is reduced, and the flow rate of the exhaust gas is limited to be reduced in comparison with the general open cell R. If the content of the PM in the exhaust gas is uniform regardless of the place, the flowing amount of the PM is smaller in a place in which the exhaust gas flow rate is smaller. Accordingly, the PM deposit quantity of the wall 2 of the open cells 3*b* of the electrodes P0 and Q0 is smaller than that of the wall 2 of the general open cell R. This fact is common to all the open cells 3*b* into which all the electrodes 5 and 6 are inserted. In FIG. 3, all the walls 2 inside the capacitor formed by the electrodes 5 and 6 are the walls 2 with the small PM deposit quantity in FIG. 4. Meanwhile, all the open cells 3*b* into which the electrodes 5 and 6 are not inserted correspond to the general open cells R described in FIG. 4, and all the walls 2 surrounding four sides are the walls 2 with the large PM deposit quantity.

As a result, the PM deposit quantity detected by the PM sensor 4 is smaller than the PM deposit quantity in the open cell R and is smaller than the average of the PM deposit quantity of the entire DPF 1.

Figure 5:
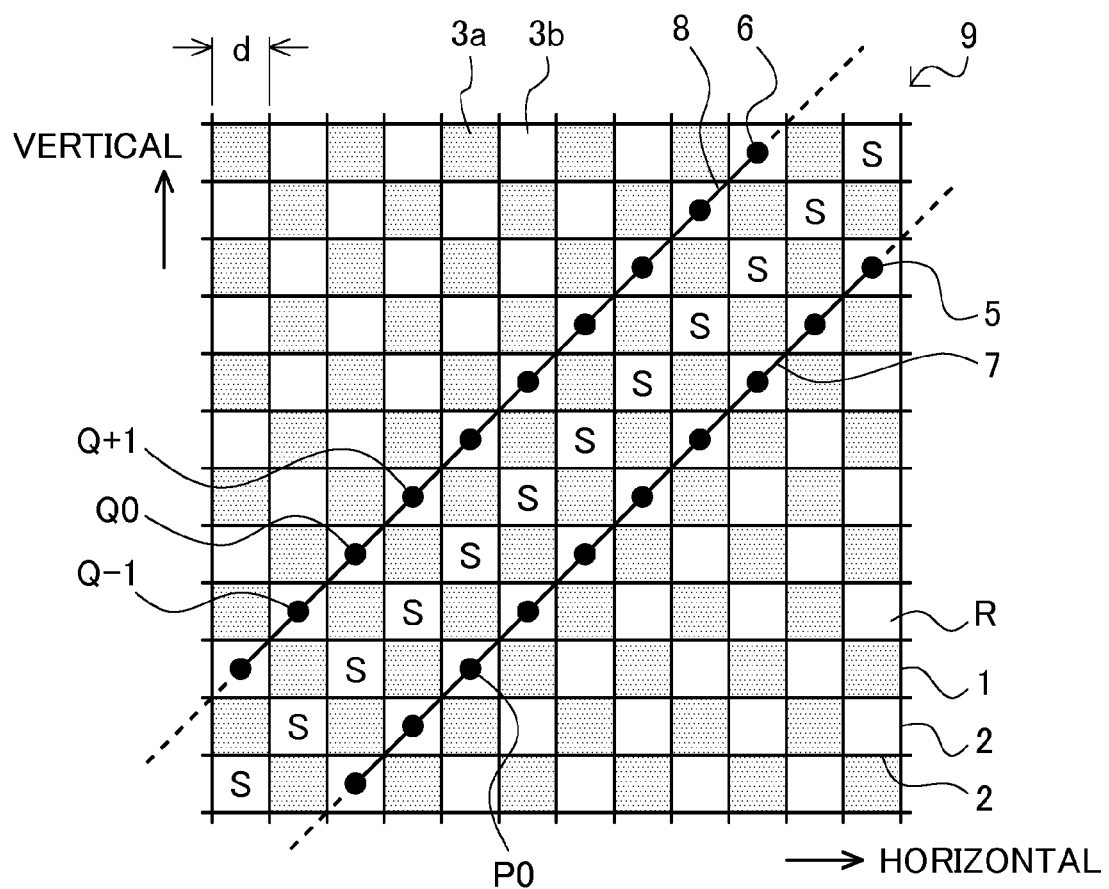
FIG. 5 is a partial end face view of the DPF to which a PM sensor of the invention is attached.

Thus, the electrode arrangement is such that the average PM deposit quantity of the entire DPF 1 can be detected. Namely, as illustrated in FIG. 5, in the PM sensor 9 of this embodiment, the first electrodes 5 are inserted into the open cells 3*b* arranged in a line in the diagonal direction, and the second electrodes 6 are inserted into the open cells 3*b* arranged in a line in the diagonal direction and including the open cells 3*b* secondarily adjacent to each of the open cells 3*b* into which the first electrodes 5 are inserted. The secondarily adjacent open cells 3*b* is the open cells 3*b* adjacent to each other by vertically and horizontally skipping over the two sealed cells 3*a* and the open cell 3*b*.

Figure 6:
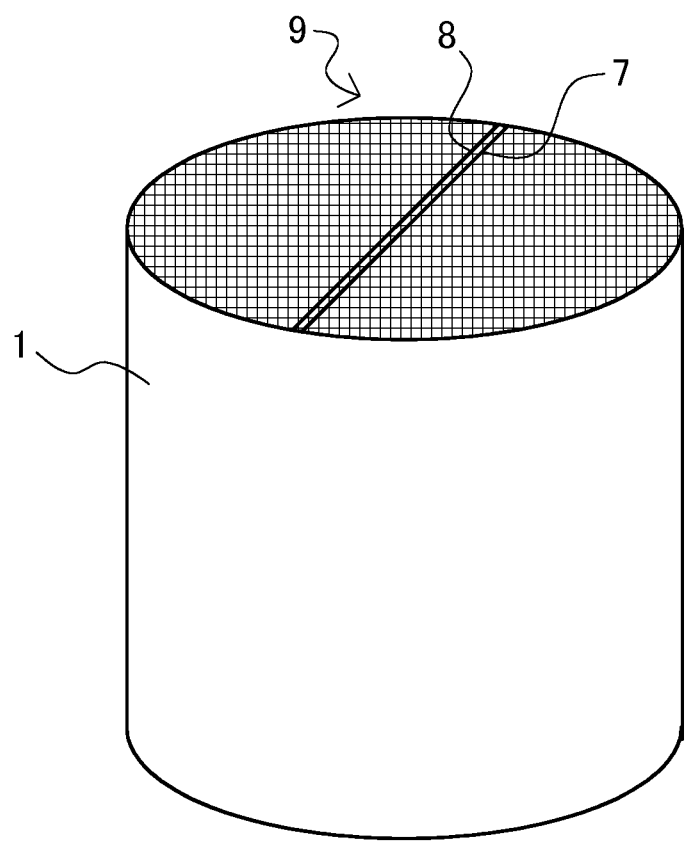
FIG. 6 is a perspective view of the DPF to which the PM sensor of the invention is attached.

As illustrated in FIG. 6, in the PM sensor 9 of this invention, the short circuiting lines 7 and 8 along the line of the open cells 3*b* into which the electrodes 5 and 6 are inserted are laid along the end face of the DPF 1. The larger the length of the line (the number of the cells 3), the greater the number of the electrodes 5 and 6, and this contributes to the increase of the facing area of the electrodes; therefore, it is preferable. For example, when the electrodes 5 and 6 are inserted into the open cells 3*b* so that the line passes near the diameter of the columnar DPF 1, the number of the electrodes 5 and 6 is maximized. For example, when the diameter of the DPF 1 is 200 mm and the pitch (vertical and horizontal widths) d of the cell 3 is 1 mm, approximately 140 cells 3 are obliquely arranged near the diameter, and therefore, the number of the open cells 3*b* into which the electrodes 5 and 6 are inserted is approximately 140.

As described above, the first and second electrodes 5 and 6 inserted into the open cells 3*b* of the DPF 1 are short-circuited by the short circuiting lines 7 and 8, and the short circuiting lines 7 and 8 are connected to a detecting circuit (not illustrated). Since the detecting circuit is similar to a conventional one, the description will be omitted.

Hereinafter, the operation of the PM sensor 9 of the present invention will be described.

When the PM is deposited on the DPF 1 of FIG. 6, also in the portion illustrated in FIG. 5, the deposit quantity of the PM deposited on the wall 2 of the cells 3 between the first electrodes 5 and the second electrodes 6 is increased. Accordingly, the capacitance of the capacitor formed by the electrodes 5 and 6 increases.

Figure 8:
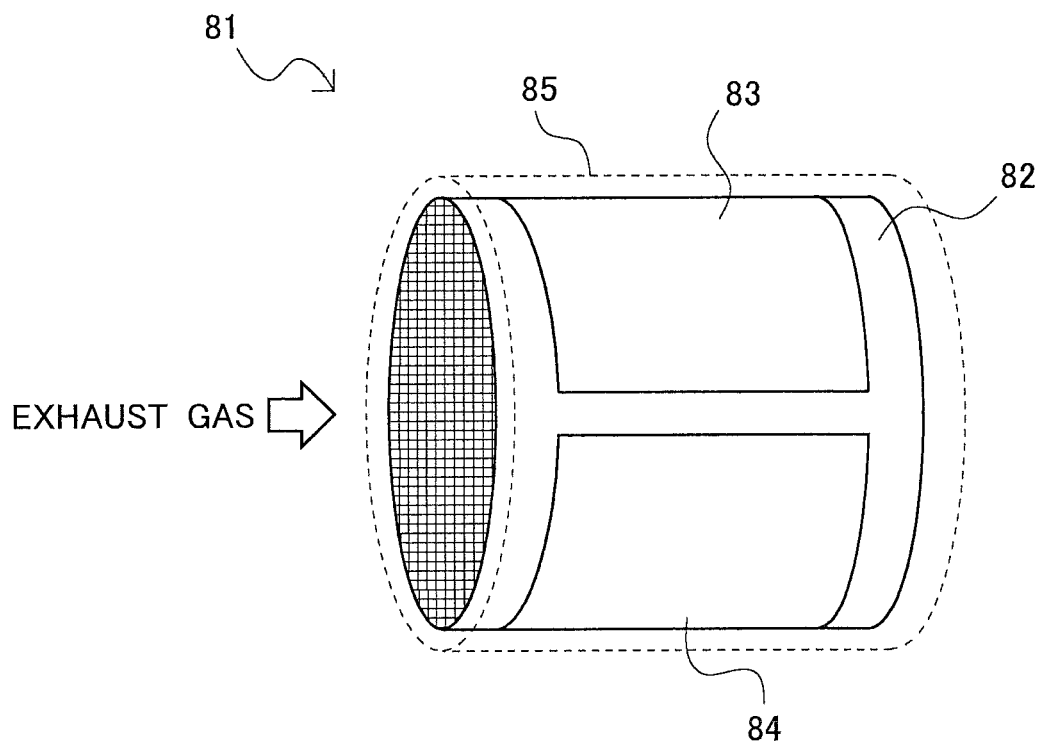
FIG. 8 is a perspective view of a conventional PM sensor.

At that time, in the PM sensor 9 of the present invention, since the open cells 3*b* inserted with the first electrodes 5 and arranged in a line in the diagonal direction and the open cells 3*b* inserted with the second electrodes 6 and arranged in a line in the diagonal direction are adjacent to each other with the two sealed cells 3*a* and the open cell provided between the electrodes, in the capacitor formed by the electrodes 5 and 6 the distance between the electrodes is $2\sqrt{2}d$, the capacitance is notably large in comparison with the capacitor formed by the electrodes 83 and 84 with the DPF 82 provided between the electrodes 83 and 84 as in the PM sensor 81 of FIG. 8. Simultaneously, in comparison with the capacitance of the capacitor formed by the electrodes 5 and 6 and the housing (not illustrated), the electrodes 5 and 6 are separated from the housing; and therefore, the capacitance of the capacitor formed by the electrodes 5 and 6 is notably large. Accordingly, the PM deposit quantity can be accurately detected.

Figure 9:
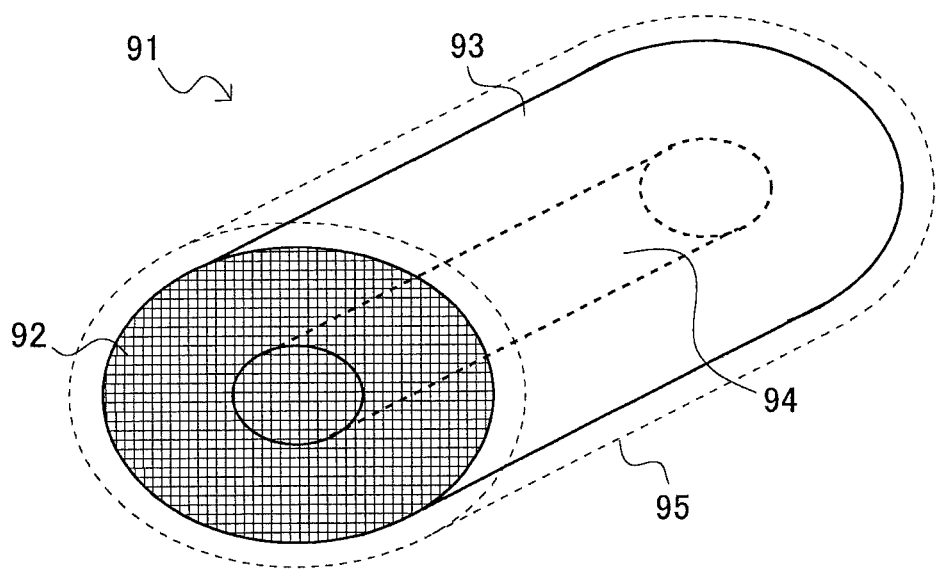
FIG. 9 is a perspective view of a conventional PM sensor.

In the PM sensor 9 of the present invention, since the electrodes 5 and 6 are inserted into the open cells 3*b* arranged in a line in the diagonal direction, the arrangement of the electrodes is different from that in the PM sensor 91 of FIG. 9 in which the electrodes 93 and 94 are arranged to be shifted near the outer circumference of a DPF 62, and in the electrode arrangement in the PM sensor 9, the electrodes 5 and 6 are arranged so as not to be shifted near the outer circumference of the DPF 1, and the average PM deposit quantity of the entire DPF 1 can be detected. In particular, as in the present embodiment, in the arrangement in which the lines of the electrodes 5 and 6 are parallel to the diameter of the DPF 1, the PM deposit quantity ranging from the central portion of the DPF 1 to the outer circumferential portion is detected.

Figure 7:
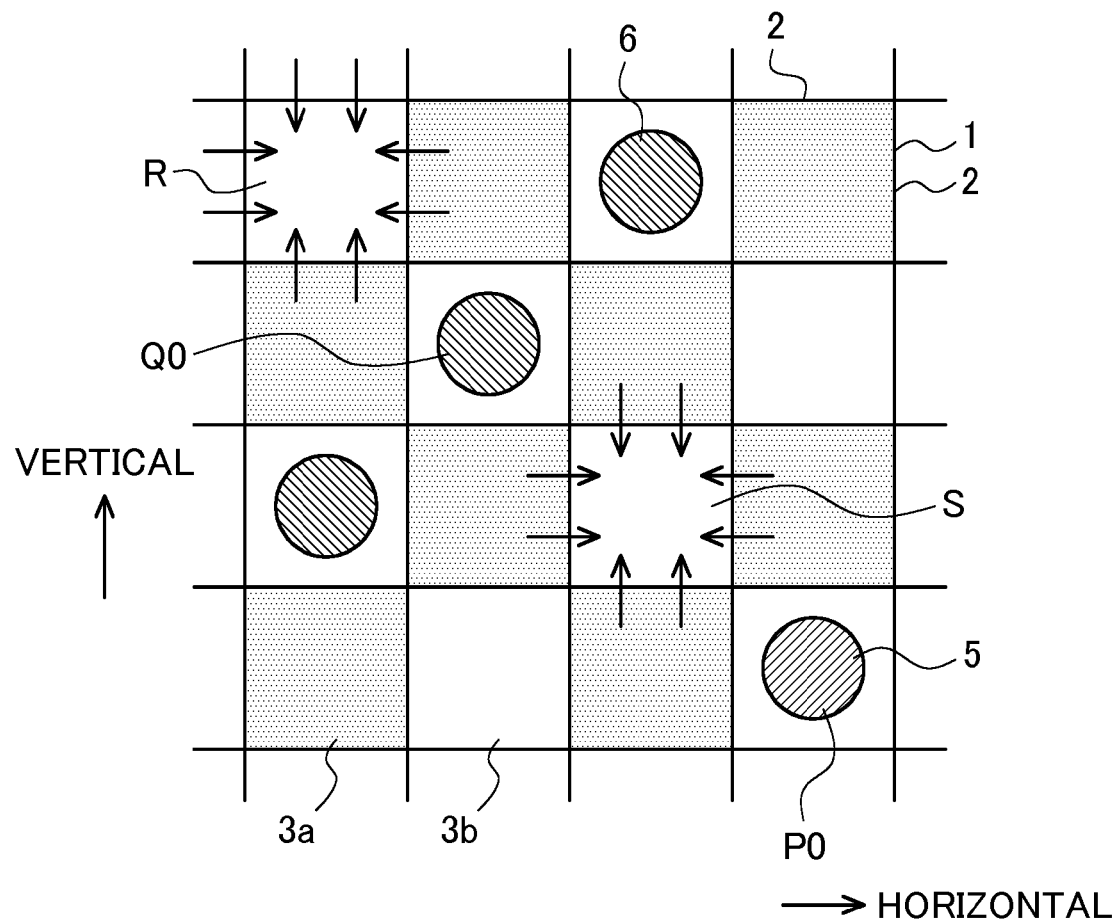
FIG. 7 is an enlarged view of a relevant portion of FIG. 5.

Further, in the PM sensor 9 of this invention, as illustrated in FIG. 7, there is the open cell 3*b* into which the electrodes 5 and 6 are not inserted between the open cell 3*b* into which the electrode P0 is inserted and the open cell 3*b* into which the electrode Q0 is inserted. Namely, the open cell 3*b* into which the electrodes 5 and 6 are not inserted exists inside the capacitor formed by the electrodes 5 and 6. This open cell 3*b* is referred to as an open cell S for detection.

The four walls 2 surrounding the open cell S for detection are the walls 2 in which the flow rate of the exhaust gas is not limited, as in the four walls 2 of the general open cell R. Accordingly, the PM deposit quantity that is the same as the amount of the open cell R is obtained in the open cell S for detection.

In FIG. 5, the open cells S for detection in which the PM deposit quantity is equivalent to that in the open cell R are arranged inside the capacitor formed by the electrodes 5 and 6. Accordingly, the PM deposit quantity detected by the PM sensor 9 can be regarded as the average PM deposit quantity of the entire DPF 1.

The invention claimed is:

1. A particulate matter sensor which detects a particulate matter deposit quantity of a diesel particulate filter based on a capacitance of a capacitor which has a plurality of first electrodes and a plurality of second electrodes inserted in a plurality of cells of the diesel particulate filter, comprising:
    the filter having an upstream face, a downstream face, and the plurality of cells stacked vertically and horizontally in a grid to extend in a direction from the upstream face to the downstream face of the filter,
    wherein the plurality of cells includes first cells that alternate with second cells in the grid,
    wherein each of the first and second cells includes a first upstream end, a second downstream end and at least one porous side wall therebetween that define a passage for a flow of fluid having the particulate matter therein through the first and second cells,
    wherein the first upstream end of each of the first cells is sealed to prevent the fluid flow therethrough, the second downstream end of each of the first cells is open to allow the fluid flow therethrough, the first upstream end of each of the second cells is open to allow the fluid flow therethrough, and the second downstream end of each of the second cells is closed to prevent the fluid flow therethrough;
    the plurality of first electrodes is arranged diagonally in the filter and is inserted into the first upstream ends of a first adjacent group of the second cells or into the second downstream ends of a second adjacent group of the first cells;
    the plurality of second electrodes, corresponding to the first plurality of electrodes, and being arranged diagonally in the filter and is inserted into one of the first upstream ends of a third adjacent group of the second cells or into the downstream ends of a fourth adjacent group of the first cells,
    wherein the first and second electrodes are all inserted at only one of the faces of the filter; and
    a third adjacent group of the second cells that corresponds to the first group and the second group,
    wherein the first electrodes, the second electrodes and the third group of second cells are parallel,
    wherein the third group is adjacent to and between the first and second groups in a direction which crosses perpendicularly a diagonal line of the diesel particulate filter where the first electrodes and the second electrodes are arranged, and
    wherein the fluid flow enters the upstream face of the filter, enters the first upstream end of the second cells, moves through the at least one porous side of the second cells, into the first cells, out the downstream ends of the first cells and out the downstream face of the filter.

2. The sensor as recited in claim 1, wherein each of the cells has a square cross section.

3. The sensor as recited in claim 1, wherein each of the cells has a circular cross section.

4. The sensor as recited in claim 1, wherein each of the cells has a rectangular cross section.

5. The sensor as recited in claim 1, wherein each of the cells has a parallelogram cross section.

6. The sensor as recited in claim 1, wherein each electrode is a metal wire.

7. The sensor as recited in claim 1, wherein each electrode terminates near an end of the cell opposite the end in which it was inserted.

8. The sensor as recited in claim 1 wherein the first electrodes are short circuited by a short circuiting line extending along one of the faces of the filter and connecting to a detecting circuit.

9. The sensor as recited in claim 1 wherein the second electrodes are short circuited by a short circuiting line extending along one of the faces of the filter and connecting to a detecting circuit.

10. The sensor as recited in claim 1, wherein the electrodes are arranged at a center of the filter.

11. The sensor as recited in claim 1, wherein the electrodes are arranged at a peripherally of the filter.

* * * * *